US00PP27047P2

(12) United States Plant Patent

Klemm et al.

(10) Patent No.: US PP27,047 P2
(45) Date of Patent: Aug. 9, 2016

(54) *PETUNIA* PLANT NAMED 'KLEPH14255'

(50) Latin Name: *Petunia hybrida*
Varietal Denomination: KLEPH14255

(71) Applicant: Klemm+Sohn GmbH & Co. KG, Stuttgart (DE)

(72) Inventors: Nils Klemm, Stuttgart (DE); Antonella Capo, Latina (IT)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 14/545,078

(22) Filed: Mar. 23, 2015

(51) Int. Cl.
*A01H 5/02* (2006.01)

(52) U.S. Cl.
USPC ..... Plt./356.23

(58) Field of Classification Search
USPC ..... Plt./356.23
CPC ..... A01H 5/02
See application file for complete search history.

*Primary Examiner* — Kent L Bell
(74) *Attorney, Agent, or Firm* — Barbara Campbell; James M. Weatherly; Cochran Freund & Young, LLC

(57) ABSTRACT

A new *Petunia* plant particularly distinguished by red flowers and an upright-mounding habit, is disclosed.

1 Drawing Sheet

Genus and species: *Petunia hybrida.*
Variety denomination: 'KLEPH14255'.

BACKGROUND OF THE NEW PLANT

The present invention comprises a new and distinct variety of *Petunia*, botanically known as *Petunia hybrida*, and hereinafter referred to by the variety name 'KLEPH14255'. 'KLEPH14255' originated from a cross-pollination conducted in July 2011 in Latina, Italy between the commercial female *Petunia* variety 'Duepotpaya' (U.S. Plant Pat. No. 22,910), also commercially known as 'Potunia Papaya' and the commercial male *Petunia* variety 'Surfinia Table Dark Red' (patent status unknown).

The seeds from the cross were sown and plants were grown in a greenhouse for evaluation, where an individual plant designated 'KLEPH14255' was selected from the group of plants in April 2012 in Latina, Italy. In April 2012, 'KLEPH14255' was first vegetatively propagated by terminal tip cuttings in Latina, Italy. 'KLEPH14255' was found to reproduce true to type in successive generations of asexual propagation via tissue culture and terminal tip cuttings.

SUMMARY

The following are the most outstanding and distinguishing characteristics of this new variety when grown under normal horticultural practices in Stuttgart, Germany and Latina, Italy.

1. Red flowers; and
2. An upright-mounding habit.

DESCRIPTION OF THE PHOTOGRAPH

This new *Petunia* plant is illustrated by the accompanying photograph of a plant grown in a glass greenhouse in Stuttgart, Germany. The photograph was taken in April 2014 and shows the foliage and flowers of a 3-month-old plant grown in a pot. The colors shown are as true as can be reasonably obtained by conventional photographic procedures.

DESCRIPTION OF THE NEW VARIETY

The following detailed descriptions set forth the distinctive characteristics of 'KLEPH14255'. The data which define these characteristics were collected from asexual reproductions carried out in Latina, Italy. Data was collected on plants grown 12-weeks from cultivation from potting in a plastic greenhouse in Latina, Italy in February 2015. Color references are to The R.H.S. Colour Chart of The Royal Horticultural Society of London (R.H.S.), $5^{th}$ edition (2007).

Classification:
- *Family.*—Solanaceae.
- *Botanical.—Petunia hybrida.*
- *Common.—Petunia.*
- *Designation.*—'KLEPH14255'.

Parentage:
- *Female parent.*—The commercial female *Petunia* variety 'Duepotpaya' (U.S. Plant Pat. No. 22,910).
- *Male parent.*—The commercial male *Petunia* variety 'Surfinia Table Dark Red' (patent status unknown).

Plant:
- *Form.*—Compact.
- *Habit.*—Upright-mounding.
- *Height (from top of soil).*—7.0 cm.
- *Width (horizontal plant diameter).*—13.0 cm.
- *Propagation.*—Terminal tip cuttings and tissue culture.
- *Time to produce a finished flowering plant.*—12 weeks in the winter under short day conditions, and 7 weeks in the spring.
- *Time to initiate and develop roots.*—2 to 3 weeks.
- *Root description.*—Moderate density, moderate branching, white roots.

Stems:
- *Average number (basal).*—12.
- *Length of basal branches (from the base of the stem to the tip).*—6.0 cm.

*Internode length.*—0.4 cm to 1.0 cm.
*Diameter of branches* (*from midpoint*).—0.4 cm.
*Stem color*.—RHS 145B.
*Anthocyanin*.—Absent.
*Texture*.—Tomentose.

Leaves:
*Arrangement*.—Alternate.
*Length.*—2.8 cm.
*Width.*—1.5 cm.
*Shape*.—Oval-elliptic.
*Apex*.—Broadly acuminate.
*Base*.—Attenuate.
*Margin*.—Entire.
*Immature leaf color*.—Upper surface: RHS N137B. Lower surface: RHS 137C.
*Mature leaf color*.—Upper surface: RHS 137B. Lower surface: RHS 137C.
*Texture* (*both upper and lower surfaces*).—Tomentose.
*Venation pattern*.—Arcuate.
*Venation color* (*both upper and lower surfaces*).—RHS 137A.
*Petioles.—Length:* 0.5 cm. Diameter: 0.3 cm. Color: RHS 145B. Texture: Tomentose.

Flower buds:
*Shape*.—Irregular oblong.
*Length.*—4.0 cm to 4.5 cm.
*Diameter.*—0.5 cm.
*Color at tight bud*.—RHS 59A.
*Texture*.—Slightly pubescent.

Inflorescence:
*Blooming habit* (*flowering season*).—Permanent flowering during summer time.
*Inflorescence type*.—Cymose.
*Lastingness of individual blooms on the plant.*—7 to 10 days.
*Fragrance*.—Absent.
*Flowers*.—Arrangement: Composed of 5 petals fused at the base. Shape: Funnel-form. Diameter (flower face): 5.5 cm. Depth (total length of flower): 5.5 cm. Throat/Funnel: Length: 3.0 cm. Diameter (at opening): 1.2 cm. Texture (both inner and outer surfaces): Smooth, glabrous. Petals: Color of petals, immature flower: Upper surface: RHS 83B. Lower surface: RHS 51B. Color of petals, mature flower: Upper surface: RHS 46B. Lower surface: RHS 51C. Apex: Broadly mucronate. Base: Fused. Margin: Entire. Strength of waviness: Weak. Degree of lobation: Medium. Calyx arrangement: Actinomorphic, composed of 5 sepals. Sepals: Color: Upper surface: RHS N137B. Lower surface: RHS 138A. Length: 1.8 cm to 2.0 cm. Width: 0.3 cm. Shape: Linear. Apex: Acute. Base: Attenuate. Margin: Entire. Texture (both upper and lower surfaces): Tomentose.
*Pedicels*.—Color: RHS 144B. Diameter: 0.2 cm. Texture: Tomentose.

Reproductive organs:
*Stamens*.—Quantity: 5. Shape: Needle with elliptic head. Filament: Length: 0.9 cm to 1.2 cm. Diameter: 0.02 cm. Color: RHS 145C. Anther: Shape: Elliptic. Color: RHS 161C. Length: 0.2 cm. Diameter: 0.15 cm. Pollen: Color: RHS 158A. Amount: Moderate.
*Pistils*.—Quantity per flower: 1. Length: 2.0 cm. Stigma color: RHS 144A. Style color: RHS 145A.

Fruit and seed set: No fruit and seed set observed.

Disease and pest/insect resistance: No disease and pest/insect resistance observed.

COMPARISON WITH PARENTAL LINES AND KNOWN VARIETY

'KLEPH14255' is a distinct variety of *Petunia* and is distinguished from its parents as described in Table 1.

TABLE 1

Comparison with Parental Lines

| Characteristic | 'KLEPH14255' | Female Parent 'Duepotpaya' | Male Parent 'Surfinia Table Dark Red' |
|---|---|---|---|
| Flower color | Red | Orange | |
| Plant habit | Upright-mounding | | Trailing |

'KLEPH14255' is a distinct variety of *Petunia* and is most similar to the commercial *Petunia* variety 'Duepotpaya' (U.S. Plant Pat. No. 22,910). Differences between the varieties are described in Table 2.

TABLE 2

Comparison with Similar Variety

| Characteristic | 'KLEPH14255' | 'Duepotpaya' |
|---|---|---|
| Flower color | Red | Orange |

We claim:

1. A new and distinct variety of *Petunia* plant designated 'KLEPH14255' as illustrated and described herein.

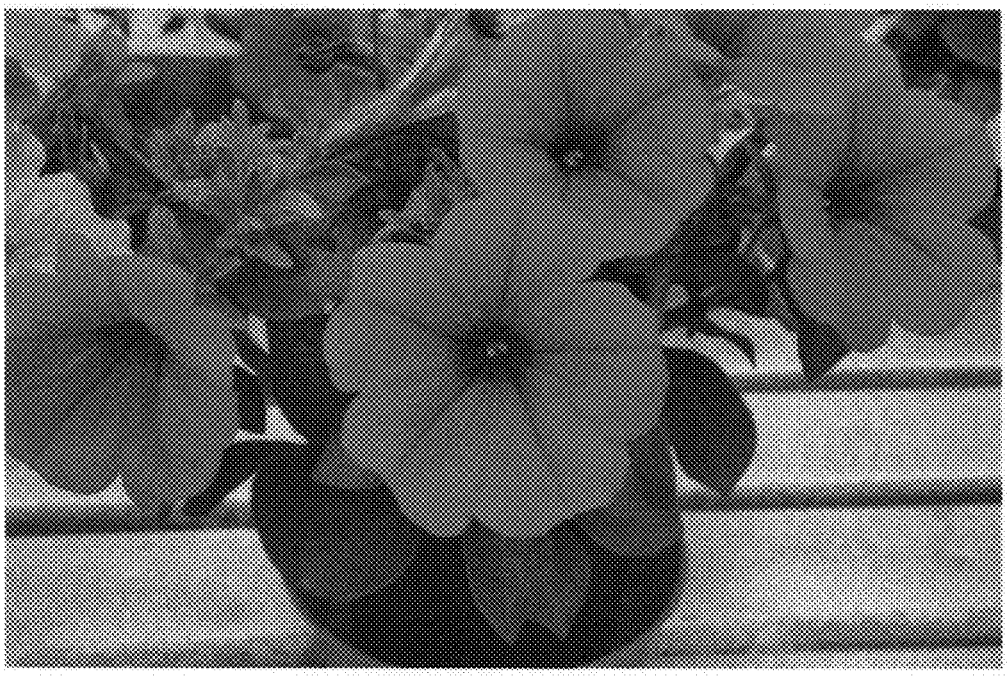

* * * * *